United States Patent
Keränen

(10) Patent No.: US 7,405,827 B2
(45) Date of Patent: Jul. 29, 2008

(54) GAS CONTENT MEASURING APPARATUS AND METHOD

(75) Inventor: Reino Keränen, Espoo (FI)

(73) Assignee: Vaisala Oyj, Helsinki (FI)

( * ) Notice: Subject to any disclaimer, the term of this patent is extended or adjusted under 35 U.S.C. 154(b) by 0 days.

(21) Appl. No.: 11/661,914

(22) PCT Filed: Sep. 8, 2005

(86) PCT No.: PCT/FI2005/000387

§ 371 (c)(1),
(2), (4) Date: Mar. 5, 2007

(87) PCT Pub. No.: WO2006/030059

PCT Pub. Date: Mar. 23, 2006

(65) Prior Publication Data

US 2008/0002205 A1    Jan. 3, 2008

(30) Foreign Application Priority Data

Sep. 14, 2004    (FI) .................................. 20041194

(51) Int. Cl.
  *G01N 21/00* (2006.01)
(52) U.S. Cl. .................. 356/432; 356/436; 356/437
(58) Field of Classification Search .............. None
  See application file for complete search history.

(56) References Cited

U.S. PATENT DOCUMENTS

| | | | |
|---|---|---|---|
| 4,657,397 A | * | 4/1987 | Oehler et al. ............... 356/414 |
| 5,201,220 A | | 4/1993 | Mullins et al. |
| 5,216,535 A | * | 6/1993 | Fellows ....................... 359/245 |
| 6,091,504 A | | 7/2000 | Walker et al. |
| 6,124,937 A | | 9/2000 | Mittenzwey et al. |
| 6,188,475 B1 | | 2/2001 | Inman et al. |
| 6,274,879 B1 | | 8/2001 | Best-Timmann |
| 6,605,804 B1 | | 8/2003 | Muller-Fiedler et al. |
| 2004/0188622 A1 | | 9/2004 | Yokura et al. |

FOREIGN PATENT DOCUMENTS

| | | |
|---|---|---|
| DE | 42 01 024 A1 | 7/1992 |
| GB | 2 391 310 A | 2/2004 |
| JP | 03068844 * | 3/1991 |
| JP | 10-267839 A | 10/1998 |
| JP | 11-287631 A | 10/1999 |
| WO | WO-99/49302 A1 | 9/1999 |

* cited by examiner

*Primary Examiner*—Michael P Stafira
(74) *Attorney, Agent, or Firm*—Birch, Stewart, Kolasch & Birch, LLP

(57) ABSTRACT

This publication discloses an apparatus and method for measuring a gas content. The apparatus includes a light transmitter (1), by means of which coherent light can be sent to the measurement object (3), a receiver (2), by means of which light that has passed through the measurement object (3) can be detected, and optical means (4, 5, 6), by means of which the light intensity of the light transmitter (1) can be aimed at the receiver (2). According to the invention, the optical means include a lens element (4), the optical axis of which is arranged essentially obliquely relative to the longitudinal axis of the measurement object (3), so that the angles of the normals of the optical boundaries relative to the measuring signal are set obliquely. The lens element (4) is both a refracting and a reflecting element, and separates the measurement object (3) from the means (1, 2, 5).

20 Claims, 1 Drawing Sheet

GAS CONTENT MEASURING APPARATUS AND METHOD

BACKGROUND OF THE INVENTION

The present invention relates to a gas content measuring apparatus, according to the preamble of claim 1.

The invention also relates to a measuring method.

Measuring apparatuses of this kind are used, for example, to measure oxygen content.

According to the prior art, measuring arrangements have been implemented, in which a coherent element is used as the light source and the path of the light is arranged, with the aid of a mirror, to travel twice through the measuring chamber. Using this arrangement brings all of the measurement electronics to the same side of the measurement channel. In solutions according to the prior art, achieving adequate measurement accuracy requires the creation of a relatively long measurement channel.

One source of measurement error is the errors caused by reflections of the coherent light signal. The reflections form diffused light, leading to variations in intensity that—particularly in the form of the interference phenomenon—disturb measurement. Reflections back to the light source are also a source of measurement error.

SUMMARY OF THE INVENTION

The invention is intended to eliminate the defects of the prior art disclosed above and for this purpose create a new type of apparatus and a significantly improved method for measuring a gas content.

The invention is based on setting the normals of all the optical surfaces obliquely relative to the direction of progression of the measurement signal, to eliminate the disturbances caused by reflections. The challenge of the invention is to implement this principal in such a way as to also meet the other requirements set for the apparatus.

In an advantageous case, the axial beam of not even one optical path lies at right angles to even one refracting optical boundary surface, including the light detector of the image plane, thus preventing the direct reflection of diffused light from the boundary surfaces to the source and the light detector. The boundary surfaces are additionally orientated in such a way that diffused light also cannot reach the source or detector indirectly, i.e. through extended reflections. For example, the angle between the normal of the first optical boundary visible from the source is greater than the spread angle of the beam of the light source, which for a light source used to measure a gas content is often considerably more than 10°. In one preferred embodiment of the invention, this general idea is implemented with the aid of a plane-convex lens and an internal mirror built into it, in which the light's path is arranged to one side of the optical axis of the plane-convex lens. In addition, collimation has been used to make the aperture of the optical arrangement significantly smaller, thus minimizing the total diameter of the measuring chamber.

More specifically, the measuring apparatus according to the invention is characterized by what is stated in the characterizing portion of claim 1.

The method according to the invention is, in turn, characterized by what is stated in the characterizing portion of claim 6.

Considerable advantages are gained with the aid of the invention.

With the aid of the invention, the errors caused by interference are minimized. At the same time however, both the transmitter and receiver elements are protected from severe measuring conditions. Using the optical arrangement according to the invention, it is possible to use economical lens components, without compromising the performance of the measuring equipment. The improvement in the performance permits a significant reduction in the size of the measuring apparatus. In some preferred embodiments of the invention, the measuring channel can be shortened to even one-third of that in solutions according to the prior art, without reducing performance.

In the following, the invention is examined with the aid of examples and with reference to the accompanying drawings.

DESCRIPTION OF THE PREFERRED EMBODIMENTS

The measuring environment according to the invention utilizes a coherent light source 1, the attenuation in the measuring channel of the light from which is monitored in the vicinity of the absorption maximum or minimum of the desired gas. The narrow spectral band of the coherent light source 1 facilitates separating the measuring signal from background light. The attenuation in the measuring channel caused by the gas being measured is thus measured in a narrow band at the spectral peak specific to the gas. The narrowness characteristic of the band can be implemented by using either a light source with a narrow band or a separate narrow-band filter located in connection with the detector, or by a combination of both.

Figure 1:
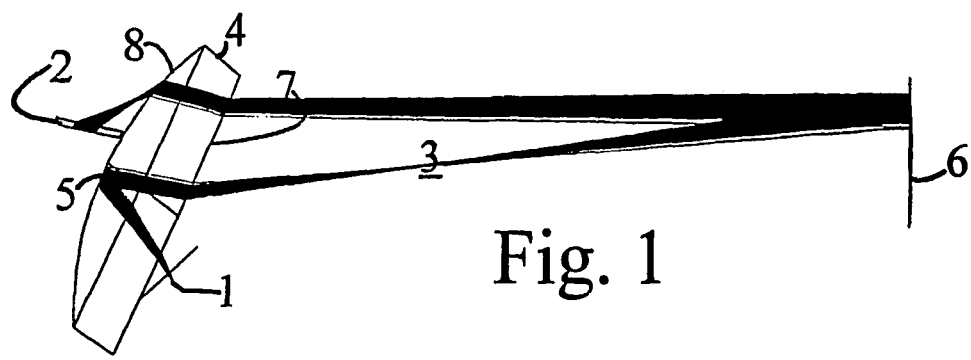
FIG. 1 shows a schematic side view of one optical arrangement according to the invention.

According to FIG. 1, the central components of the measuring apparatus according to the invention are a plane-convex lens 4, on the plane surface of which a coherent light source 1 is located. The light source aligns its beam obliquely to the plane surface 7 of the lens 4, thus avoiding feedback of the light to the light source 1. In the example of the figure, the angle of incidence of the beam is 25 degrees relative to the normal of the plane 7, so that feedback 12 at the spread angle of the degree (FWHM) to the radiating source is prevented at a confidence level of more than four standard deviations. A reflector surface 5, to which the light beam is focussed after passing through the plane surface 7 of the lens 4, is created on the concave surface 8 of the lens 4. The reflector surface 5 thus acts as a concave internal mirror. The size and shape of the reflector surface 5 can be used to define the size and shape of the beam that it reflects. The collimation of the beam is controlled by the convexity of the surface 8.

From the reflector surface 5 the beam continues towards the plan surface 7 of the lens 5, which it intersects obliquely, the central beam in the example of the figure being at 22 degrees relative to the normal of the plane 7, and continues to the measuring channel 3. At the end of the measuring channel 3, the measuring signal is reflected and focussed back from the concave mirror 6 to the plane surface 7. In the example of the figure, the centre beam is at a angle of incidence of 31 degrees relative to the normal of the plane 7. The measuring signal continues to travel to the convex surface 8, which is also oblique, in the example of the figure the centre beam being at an angle of incidence of 34 degrees relative to the normal of the surface. From the surface 8, the beam proceeds to the detector 2 set obliquely, which in the example case the centre beam intersects at an angle of incidence of 46 degrees.

Using the geometry shown, more than 66% of the vertically polarized light transmitted from the light source is transferred to the surface of the detector 2, by means of which 93% of the oval point of light is absorbed on the detector surface, which in the example case has a surface area of 2.5×5.0 mm². Transmission losses occur in the optical boundary surfaces and in the aperture defined by the mirror 5, the surface area of which in the example case of the figure is 38.5 mm².

The arrangement attenuates the progression of the horizontally polarized light, which property can be exploited if the light source 1 is clearly polarized.

Figure 2:
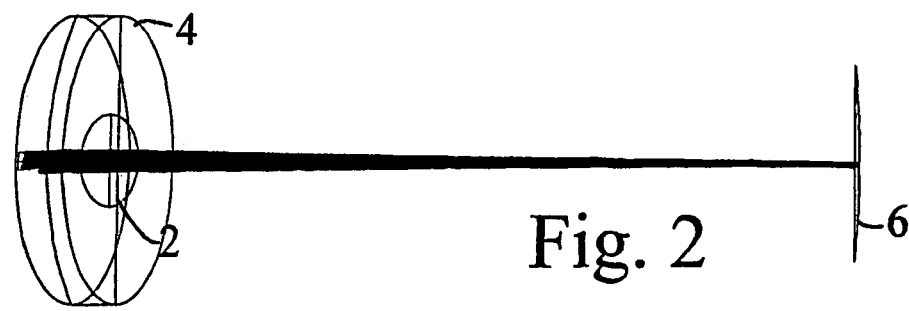
FIG. 2 shows a bottom view of the optical arrangement of FIG. 1.

According to FIG. 2, the path of the measuring signal lies essentially on a plane and in this projection all the optical components are at right angles, which facilitates manufacture of the apparatus.

Figure 3:
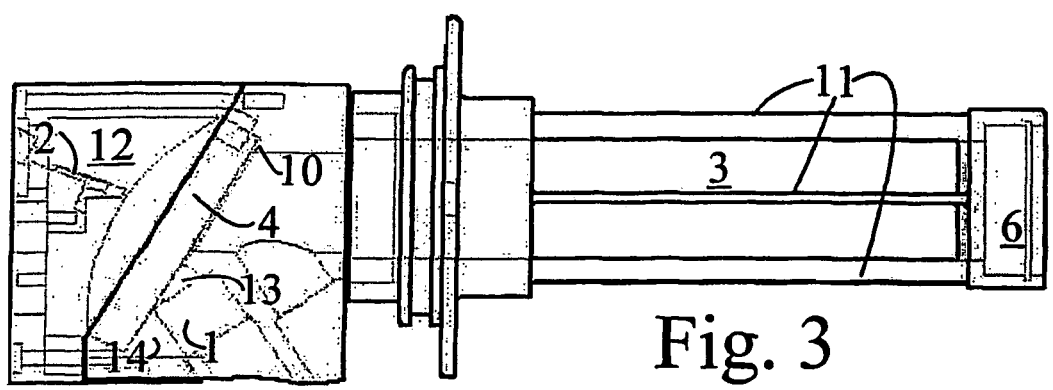
FIG. 3 shows a side view of the equipment implementation according to FIG. 1, together with its support structures.

FIG. 3 shows the mechanical construction of the measuring device in greater detail. According to the figure, an instrument chamber 12, which is gas-tightly separated from the measuring channel 3, is created behind the lens 4. The plane surface 7 of the lens 4 is sealed from the measuring channel 3 with an O-ring. The mirror 6 is protected with a protective layer, because the chemical environment of the measuring channel is often corrosive and/or oxidizing. The protective layer is typically of silicon oxide (SiO), silicone nitride, or magnesium fluoride (MgF). The other components liable to be damaged are separated from the gas being measured with the aid of the lens 4, so that there is no need to protect them separately. An open measuring channel 3 is formed inside support rods 11. The mirror 6 is located at the end of the support rods 11. The length of the light path in the measuring channel is typically 30 cm, so that the support rods about 10-cm long. The material of the support rods 11 is typically stainless steel. In front of the detector 1 there is a chamber 13, which can be used as a reference-gas chamber. A constant content of a known gas can be arranged in this chamber, or correspondingly, for example when measuring oxygen, it can be kept at the content of the surrounding air, as there is little variation in oxygen content in normal air. A cooling element with a high thermal conductivity is arranged near the light source 1, to conduct heat away from the light source 1. All dimensional tolerances in the optical arrangement can be realized using conventional machining methods (±0.1 mm).

In the example case, the measuring channel has a diameter of 25 mm and the measuring light beam is aligned so that it will not strike the walls or support rods.

For the best possible absorption of undesired reflections, the apparatus is equipped with black surfaces at the end points of the diffusion paths. Possible diffusion beams and their reflection points can be determined using existing methods.

Figure 4:
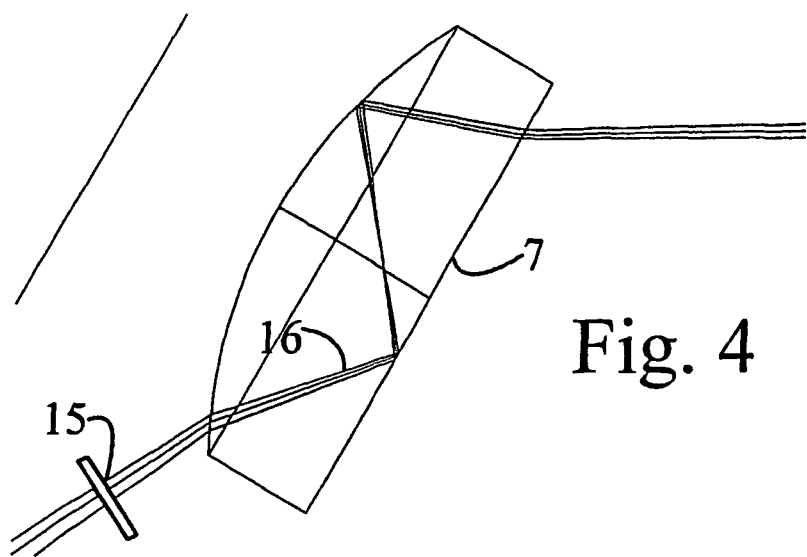
FIG. 4 shows a side view of the optical components according to the invention and one path of diffused light in it.

FIG. 4 shows an example of one potentially detrimental light path, which in this case is prevented from proceeding to the light source with the aid of total reflection. In a preferred optical arrangement, six other similar diffuse light paths appear—corresponding to each refracting optical surface and the diffuse light paths proceeding from them—are prevented both from proceeding to the light detector and back to the source. According to FIG. 4, the signal arising from the diffuse light can be exploited and an additional detector 15 can be arranged at the lower edge of the lens 4 to measure the intensity of the horizontally polarized light 16. The total reflection of the plane surface 7 creates the light path shown in the figure.

The mirror 5 can be made semi-translucent and an additional detector (not shown) can be placed obliquely in the space 12 behind the mirror 5. With the aid of the second detector, the intensity of the light of the source can then be monitored and thus information obtained, for example, on the dirtying of the mirror 6 and the plane surface 7 and on the aging and drift of the light source 1.

The lens 4 is typically tilted at an angle of about 40-80, preferably about 60 degrees, relative to the longitudinal axis of the measuring channel 3.

In a preferred embodiment of the invention, the beam of light is arranged at an angle of at least 10 degrees to the normal of the plane surface 7.

The invention claimed is:

1. Apparatus measuring a gas content, which apparatus includes
   a light transmitter (1), by means of which coherent light can be sent to the measurement object (3),
   a receiver (2), by means of which light that has passed through the measurement object (3) can be detected, and
   optical means (4, 5, 6), by means of which the light intensity of the light transmitter (1) can be aimed at the receiver (2),
characterized in that
   the optical means include a lens element (4), through which both the transmitted and received light is adapted to pass and the optical axis of which is arranged essentially obliquely relative to the longitudinal axis of the measurement object (3), so that the angles of the normals of the optical boundaries relative to the measuring signal are set obliquely,
   the lens element (4) is both a refracting and a reflecting element, and
   the lens element (4) separates the measurement object (3) from the components (1, 2, 5) liable to dirtying and wear.

2. Apparatus according to claim 1, characterized in that the optical means consist of lens elements (4), on the first side of which the light source (1) is located, from which the path of the light is arranged to travel through the lens element (4) to a mirror (5) on the opposite side of it, and from this on through the measurement object (3) once again through the lens element (4) to the detector (2) located on the second side of it.

3. Apparatus according to claim 1, characterized in that the lens element (4) is planar on the side facing the measurement object (3) and convex on the side facing the detector (2).

4. Apparatus according to claim 1, characterized in that the path of the light is arranged at an angle of at least 10 degrees relative to the normals of the planar surfaces (7) of the optical elements.

5. Apparatus according to claim 1, characterized in that the optical axis of the lens component (4) is arranged obliquely relative to the measuring channel (3), preferably at an angle of about 60 degrees relative to the longitudinal axis of the measuring channel.

6. Apparatus according to claim 1, characterized in that the light transmitter (1) and the receiver (2) are located close to each other on opposite sides of the same optical component (4).

7. Apparatus according to claim 1, characterized in that the optical component (4) acting as a window of the measuring chamber is used as an internal mirror and as a convex lens, and the optical axis of the optical component (4) is set at a significantly obliquely relative to the longitudinal axis of the measuring channel (3).

8. Method for measuring a gas content, in which method coherent light is sent to the measurement object (3),
   the light is directed using optical means (4, 5, 6), and the light passing through the measurement object is detected, characterized in that the optical means include a lens element (4), through which both the transmitted and received light is adapted to pass and the optical axis of which is arranged essentially obliquely relative to the longitudinal axis of the measurement object (3), so that the angles of the normals of the optical boundaries relative to the measuring signal are set obliquely, the lens element (4) is used as both a refracting and a reflecting element, and the lens element (4) is used to separate the measurement object (3) from the components (1, 2, 5) liable to dirtying and wear.

9. Method according to claim 8, characterized in that the optical means consist of lens elements (4), on the first side of which the light source (1) is located, from which the path of the light is arranged to travel through the lens element (4) to a mirror (5) on the opposite side of it, and from this on through the measurement object (3) once again through the lens element (4) to the detector (2) located on the second side of it.

10. Apparatus according to claim 8, characterized in that the lens element (4) is selected in such a way that it is planar on the side facing the measurement object (3) and convex on the side facing the detector (2).

11. Apparatus according to claim 8, characterized in that the path of the light is arranged at an angle of at least 10 degrees relative to the normals of the planar surfaces (7) of the optical elements.

12. Apparatus according to claim 8, characterized in that the optical axis of the lens component (4) is arranged obliquely relative to the measuring channel (3), preferably at an angle of about 60 degrees relative to the longitudinal axis of the measuring channel.

13. Apparatus according to claim 8, characterized in that the light transmitter (1) and the receiver (2) are located close to each other on opposite sides of the same optical component (4).

14. Apparatus according to claim 8, characterized in that the optical component (4) acting as a window of the measuring chamber is used as an internal mirror and as a convex lens, and the optical axis of the optical component (4) is set significantly obliquely relative to the longitudinal axis of the measuring channel (3).

15. Apparatus according to claim 2, characterized in that the lens element (4) is planar on the side facing the measurement object (3) and convex on the side facing the detector (2).

16. Apparatus according to claim 2, characterized in that the path of the light is arranged at an angle of at least 10 degrees relative to the normals of the planar surfaces (7) of the optical elements.

17. Apparatus according to claim 3, characterized in that the path of the light is arranged at an angle of at least 10 degrees relative to the normals of the planar surfaces (7) of the optical elements.

18. Apparatus according to claim 2, characterized in that the optical axis of the lens component (4) is arranged obliquely relative to the measuring channel (3), preferably at an angle of about 60 degrees relative to the longitudinal axis of the measuring channel.

19. Apparatus according to claim 3, characterized in that the optical axis of the lens component (4) is arranged obliquely relative to the measuring channel (3), preferably at an angle of about 60 degrees relative to the longitudinal axis of the measuring channel.

20. Apparatus according to claim 4, characterized in that the optical axis of the lens component (4) is arranged obliquely relative to the measuring channel (3), preferably at an angle of about 60 degrees relative to the longitudinal axis of the measuring channel.

* * * * *